US005693811A

United States Patent [19]

Lindstrom

[11] Patent Number: 5,693,811
[45] Date of Patent: Dec. 2, 1997

[54] PROCESS FOR PREPARING TETRAHDROIMIDAZOQUINOLINAMINES

[75] Inventor: Kyle J. Lindstrom, Houlton, Wis.

[73] Assignee: Minnesota Mining and Manufacturing Company, St. Paul, Minn.

[21] Appl. No.: 669,895

[22] Filed: Jun. 21, 1996

[51] Int. Cl.$^6$ ............................................. C07D 401/14
[52] U.S. Cl. ............................................. 546/82; 546/64
[58] Field of Search ........................................ 546/82, 64

[56] References Cited

U.S. PATENT DOCUMENTS

| | | | |
|---|---|---|---|
| 3,764,681 | 10/1973 | Dreikorn | 424/258 |
| 3,891,653 | 6/1975 | Dreikorn | 260/288 |
| 4,689,338 | 8/1987 | Gerster | 514/293 |
| 4,698,348 | 10/1987 | Gerster | 514/293 |
| 4,988,815 | 1/1991 | Andre et al. | 546/159 |
| 5,175,296 | 12/1992 | Gerster | 546/82 |
| 5,266,575 | 11/1993 | Gerster et al. | 514/293 |
| 5,268,376 | 12/1993 | Gerster | 514/293 |
| 5,346,905 | 9/1994 | Gerster | 514/293 |
| 5,352,784 | 10/1994 | Nikolaides et al. | 594/126 |
| 5,367,076 | 11/1994 | Gerster | 546/82 |
| 5,389,640 | 2/1995 | Gerster et al. | 514/293 |
| 5,395,937 | 3/1995 | Nikolaides et al. | 546/82 |
| 5,444,065 | 8/1995 | Nikolaides et al. | 514/293 |

FOREIGN PATENT DOCUMENTS 90.301776.3  9/1990  European Pat. Off. .

OTHER PUBLICATIONS

Fu, P.P.,et al. "Regioselective Catalytic Hydrogenation of Polycyclic Aromatic Hydrocarbons under Mild conditions" J. Org. Chem., 45, pp. 2797–2803, 1980.

Houben–Weyl, "Methoden der Organischen Chemie", vol. IV/1c, pp. 271–279 (1980) (with translation).

Chemistry of Heterocylic Compounds (English Edition) 1981, 16, (12), 1286–1288 (Zyryanov).

*Primary Examiner*—C. Warren Ivy
*Assistant Examiner*—Lyman H. Smith
*Attorney, Agent, or Firm*—Gary L. Griswold; Walter N. Kirn; Ted K. Ringsred

[57] ABSTRACT

A process for preparing 6, 7, 8, 9-tetrahydro-1H-imidazo[4,5-c]quinolin-4-amines is disclosed. The process involves the reduction of a 1H-imidazo[4,5-c]quinolin-4-amine or of a 6H-imidazo[4,5-c]tetrazolo[1,5-a]quinoline.

14 Claims, No Drawings

PROCESS FOR PREPARING TETRAHDROIMIDAZOQUINOLINAMINES

BACKGROUND OF THE INVENTION

1. Technical Field

This invention relates to processes for preparing 6,7,8,9-tetrahydro-1H-imidazo[4,5-c]quinolin-4-amines.

2. Description of the Related Art

Certain immonomodulator 6,7,8,9-tetrahydro-1H-imidazo[4,5-c]quinolin-4-amines and methods for their preparation are known and disclosed in U.S. Pat. No. 5,532,784 (Nikolaides). The methods disclosed involve starting with either a cyclic β-ketoester or a 5,6,7,8-tetrahydro-4-hydroxy-3-nitro-2(1H)-quinolinone and building the remainder of the molecule.

SUMMARY OF THE INVENTION

This invention provides a process for preparing a compound of Formula I

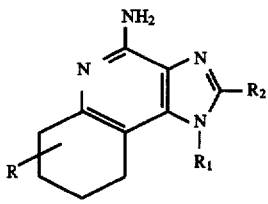

wherein $R_1$ is selected from the group consisting of hydrogen; cycloalkyl of three, four, or five carbon atoms, straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycoalkyl containing three to about six carbon atoms substituted by straight chain or branched chain alkyl containing one to about four carbon atoms; hydroxyalkyl of one to about six carbon atoms; alkoxyalkyl wherein the alkoxyl moiety contains one to about four carbon atoms and the aklyl moiety contains two to about six carbon atoms; acyloxyalkyl wherein the acyloxy moiety is alkanoyloxy of two to about four carbon atoms or benzoyloxy, and the alkyl moiety contains one to about six carbon atoms; aminoalkyl of one to about four carbon atoms; morpholinoalkyl wherein the alkyl moiety contains two to about four carbon atoms;

$R_2$ is selected from the group consisting of hydrogen, straight chain or branched chain alkyl containing one to about eight carbon atoms and —C($R_S$)($R_T$)(X)

wherein $R_S$ and $R_T$ are independently selected from the group consisting of hydrogen and alkyl of one to about four carbon atoms, X is selected from the group consisting of alkoxy containing one to about four carbon atoms, alkoxyalkyl wherein the alkoxyl moiety contains one to about four carbon atoms and the alkyl moiety contains one to about four carbon atoms, alkylamido wherein the alkyl group contains one to about four carbon atoms, amino, substituted amino wherein the substituent is alkyl or hydroxyalkyl of one to about four carbon atoms, and morpholinoalkyl wherein the alkyl moiety contains one to about four carbon atoms, and R is selected from the group consisting of hydrogen, straight chain or branched chain alkyl containing one to about four carbon atoms; comprising the steps of:

(i) providing a compound of Formula II

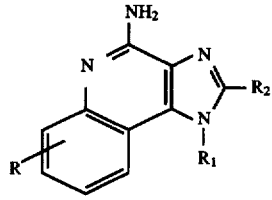

wherein R, $R_1$, and $R_2$ are as defined above;

(ii) reducing a solution or suspension of the compound of Formula II in a strong acid in the presence of platinum (IV) oxide under hydrogen pressure;

(iii) isolating the compound of Formula I or a pharmaceutically acceptable addition salt thereof.

This invention also provides a process for preparing a compound of Formula I

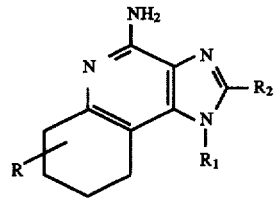

wherein R, $R_1$ and $R_2$ are as defined above, comprising the steps of:

(i) providing a compound of Formula III

wherein R, $R_1$, and $R_2$ are as defined above;

(ii) reducing a solution or suspension of the compound of Formula III in trifluoroacetic acid in the presence of platinum (IV) oxide under hydrogen pressure;

(iii) isolating the compound of Formula I or a pharmaceutically acceptable addition salt thereof.

DETAILED DESCRIPTION OF THE INVENTION

Substituents designated parenthetically herein indicate that the substituent is optionally present, e.g., a 4-(substituted) amino compound contains either an unsubstituted 4-amino group or a substituted 4-amino group.

Reaction Scheme I illustrates a process of the invention. Compounds of Formula II and methods for their preparation are known and disclosed, e.g., in European Patent Application 90.301776.3, U.S. Pat. Nos. 4,689,338 (Gerster), 4,988, 815 (Andre), 5,175,296 Gerster), 5,266,575 (Gerster), 5,376, 976 (Gerster), 5,389,640 (Gerster) and 5,395,937 (Nikolaides) all seven patents being incorporated herein by reference.

Reaction Scheme I

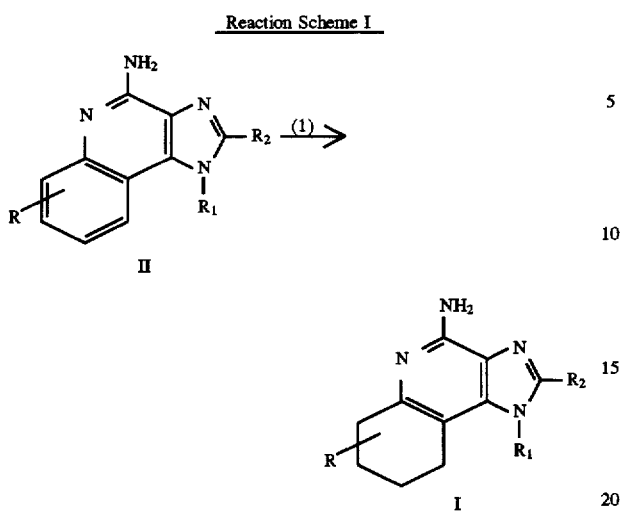

Reaction Scheme II, wherein R, $R_1$ and $R_2$ are as defined above, illustrates a process of the invention. The unsubstituted compound of Formula IV is a known compound and other compounds of Formula IV can be prepared by methods known to those skilled in the art and disclosed, e.g., in *Chemistry of Heterocyclic Compounds* (English Edition), 1981, 16, (12), 1286–1288 (Zyryanov).

In step (1) of Reaction Scheme I a 4-amino-6,7,8,9-tetrahydro-1H-imidazo[4,5-c]quinoline of Formula I is provided by reducing a 4-amino-1H-imidazo[4,5-c]quinoline of Formula II. The reduction is carried out by suspending or dissolving a compound of Formula II in trifluoroacetic acid adding a catalytic amount of platinum (IV) oxide, then subjecting the mixture to hydrogen pressure [25 to 100 psi $(1.72\times10^5$ to $6.89\times10^5$ Pa)]. Optionally, a solvent such as ethanol may be included. The preferred method is to use trifluoroacetic acid without any additional solvent. The reaction may conveniently be carried out in Paar apparatus. The product or a pharmaceutically acceptable addition salt thereof is isolated using conventional methods.

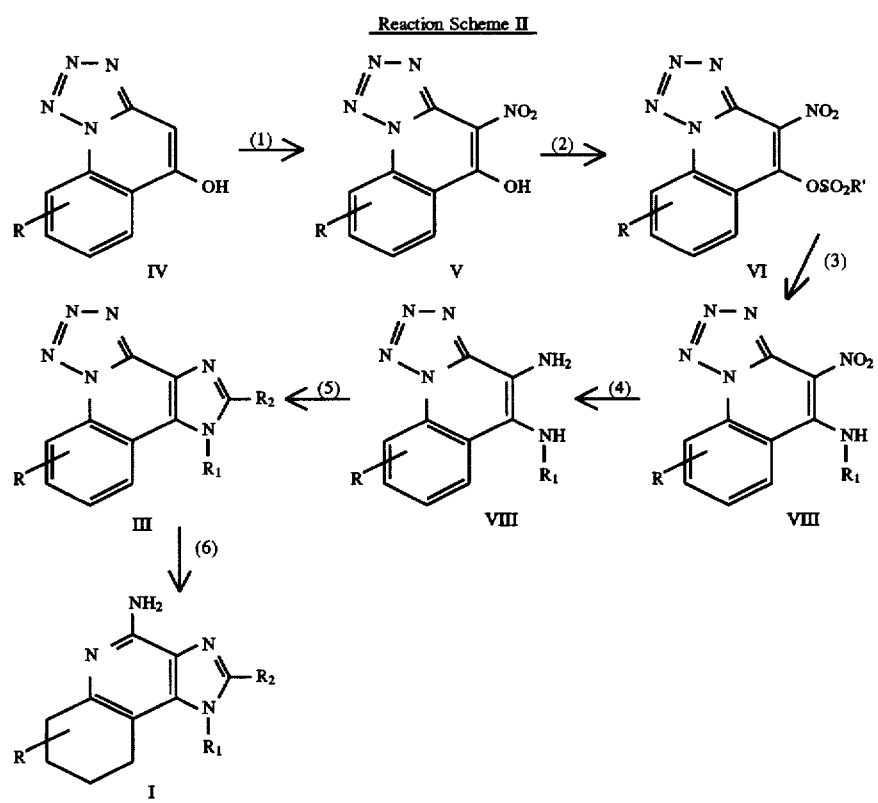

Reaction Scheme II

In step (1) of Reaction Scheme II a 4-nitrotetrazolo[1,5-a]quinolin-5-ol of Formula V is provided by nitrating a tetrazolo[1,5-a]quinolin-5-ol of Formula IV. Conventional conditions for such reaction are well known. Preferred conditions in the instance where R is hydrogen involve heating in acetic acid in the presence of nitric acid. Preferred conditions in other instances will depend upon the particular tetrazolo[1,5-a]quinolin-5-ol used, and those skilled in the art will be able to select suitable conditions. The product can be isolated from the reaction mixture using conventional methods.

In step (2) of Reaction Scheme II a 4-nitrotetrazolo[1,5-a]quinolin-5-sulfonate of Formula VI is provided by reacting a 4;-nitrotetrazolo[1,5-a]quinolin-5-ol of Formula V with a sulfonyl halide or preferably a sulfonic anhydride. Suitable sulfonyl halides include alkylsulfonyl halides such as methanesulfonyl chloride and trifluoromethanesulfonyl chloride, and arylsulfonyl halides such as benzenesulfonyl chloride, p-bromobebzenesulfonyl chloride and p-toluenesulfonyl chloride. Suitable sulfonic anhydrides include those corresponding to the above-mentioned sulfonyl halides. Sulfonic anhydrides are preferred in view of the fact that the sulfonate anion generated as a by-product of the reaction is a relatively poor nucleophile and as such does not give rise to undesired side products such as those in which the nitro group is displaced. A particularly preferred sulfonic anhydride is trifluoromethanesulfonic anhydride.

The reaction is preferably carried out by combining a compound of Formula V with a base, preferably an excess of a tertiary amine base (e.g., a trialkylamine base such as triethyl amine) in a suitable solvent such as dichloromethane and then adding the sulfonyl halide of sulfonic anhydride. The addition is preferably carried out in a controlled fashion (e.g., dropwise) and at a reduced temperature (e.g., about 0° C.). The product can be isolated by conventional methods or it can be carried on without isolation as described below in connection with step(3).

In step (3) of Reaction Scheme II a 4-nitrotetrazolo[1,5-a]quinolin-5-amine of Formula VII is provided by reacting a 4-nitrotetraozolo[1,5-a]quinolin-5-sulfonate of Formula VI with an amine, preferably in the presence of an excess of an amine base in a solvent such as dichloromethane. Suitable amines include ammonia and preferably primary amines. Primary amines provide 5-substituted amino compounds of Formula VII wherein the amino substituent is represented by $R_1$. Particularly preferred amines include isobutylamine and 2-aminomethyl-2-propanol.

The reaction can be carried out by adding an excess of amine to the reaction mixture resulting from Step (2). The reaction can also be carried out by adding an excess of amine to a solution of the compound of Formula VI in a solvent such as dichloromethane. As the sulfonate is a relatively facile leaving group the reaction can be run at ambient temperature. The product can be isolated from the reaction mixture using conventional methods.

In step (4) of Reaction Scheme II a tetrazolo [1,5-a] quinolin-4,5-diamine of Formula VIII is provided by reducing a 4-nitrotetrazolo[1,5-a]quinolin-5-amine of Formula VII. Methods for such reduction are well know to those skilled in the art. Preferably the reduction is carried out using a conventional heterogeneous hydrogenation catalyst such as platinum on carbon or palladium on carbon. The reduction can be conveniently carried out on a Paar apparatus in a solvent such as ethanol. The product can be isolated from the reaction mixture using conventional methods.

In step (5) of Reaction Scheme II a 6H-imidazo[4,5-c] tetrazolo[1,5-a]quinoline of Formula III is provided by reacting a tetrazolo[1,5-a]quinolin-4,5-diamine of Formula VIII with a carboxylic acid or an equivalent thereof. Suitable equivalents to carboxylic acid include acid halides, orthoesters, and 1,1-dialkoxyalkyl alkanoates. The carboxylic acid or equivalent is selected such that it will give rise to the desired 6-substituent in the compound of Formula III wherein the 6-substituent is designated $R_2$ (e.g., acetyl chloride will give rise to a compound where $R_2$ is methyl). The reaction can be run in the absence of solvent or preferably in an inert solvent in the presence of a carboxylic acid or equivalent thereof with sufficient heating to drive off any alcohol or water formed as a side product of the reaction. The product can be isolated from the reaction mixture using conventional methods.

In step (6) of Reaction Scheme II a 4-amino-6,7,8,9-tetrahydro-1H-imidazo[4,5-c]quinoline of Formula I is provided by reducing a 6H-imidazo[4,5-c]tetrazolo[1,5-a] quinoline of Formula III. The reduction is carried out by suspending or dissolving a compound of Formula III in trifluoroacetic acid, adding a catalytic amount of platinum (IV) oxide, then subjecting the mixture to hydrogen pressure [25 to 100 psi($1.72 \times 10^5$ to $6.89 \times 10^5$Pa)]. Optionally, a solvent such as ethanol may be included. The preferred method is to use trifluoroacetic acid without an additional solvent. The reaction may conveniently be carried out in a Paar apparatus. The product or a pharmaceutically acceptable addition salt thereof is isolated using conventional methods.

In Reaction Scheme II, R' can be any group that can be incorporated into a sulfonyl halide or a sulfonic anhydride. Alkyl (e.g., methyl), haloalkyl including perfluoroalkyl (e.g., trifluoromethyl) and aryl (e.g., phenyl, halophenyl and tolyl) are all suitable.

Reaction Scheme III, wherein R, $R_1$ and $R_2$ are as defined above, illustrates a process of the invention. Compounds of Formula IX and methods for their preparation are known and disclosed, e.g., in U.S. Pat. Nos. 4,988,815 (Andre), and 5,268,376 (Gerster), both patents being incorporated herein by reference.

Reaction Scheme III

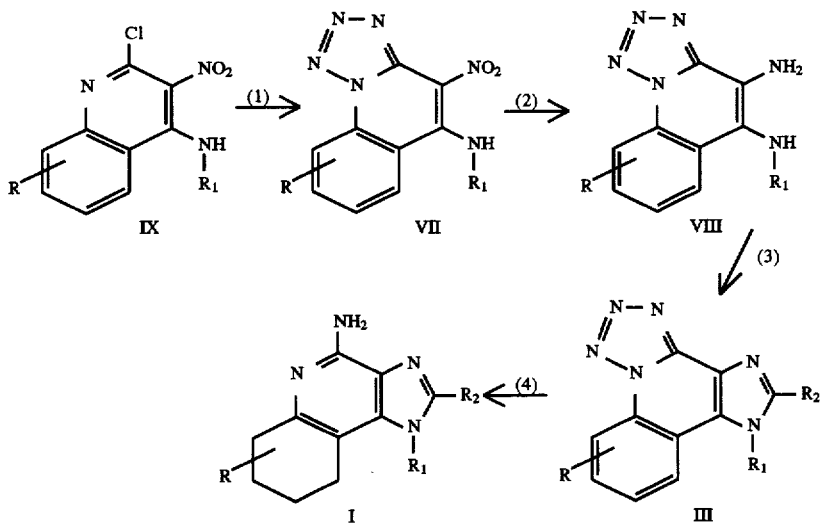

In step (1) of Reaction Scheme III a 4-nitrotetrazolo[1,5-a]quinolin-5-amine of Formula VII is provided by reacting a (4-substituted) amino-2chloro-3-nitroquinoline of Formula IX with sodium azide. The reaction can be carried out by combining the compound of Formula IX with sodium azide in a suitable solvent such as N,N-dimethylformamide and heating (about 50° C.). The product can be isolated from the reaction mixture using conventional methods.

Steps (2), (3) and (4) of Reaction Scheme III can be carried out in the same manner as steps (4), (5) and (6) of Reaction Scheme II respectively.

Reaction Scheme IV, wherein R, $R_1$ and $R_2$ are as defined above, illustrates a process of the invention. Compounds of Formula X and methods for their preparation are known and disclosed, e.g., in European Patent Application 90.301776.3, U.S. Pat Nos. 4,689,338 (Gerster), 4,698,348 (Gerster), 4,988,815 (Andre), and 5,389,640 (Gerster) all four patents being incorporated herein by reference.

In step (1) of Reaction Scheme IV a 4-hydrazino-1H-imidazo[4,5-c]quinoline of Formula XI is provided by reacting a 4-chloro-1H-imidazo[4,5-c]quinoline of Formula X with hydrazine. The reaction can be carried out by combining a compound of Formula X with an excess of hydrazine and heating if necessary. The product can be isolated from the reaction mixture using conventional methods.

In step (2) of Reaction Scheme IV a 6H-imidazo[4,5-c]tetrazolo[1,5-a]quinoline of Formula III is provided by reacting a 4-hydrazino-1H-imidazo[4,5-c]quinoline of Formula XI with sodium nitrite. The reaction can be carried out by combining the compound of Formula XI with sodium nitrite in a suitable solvent (e.g., water) in the presence of an acid (e.g., acetic acid). The product can be isolated from the reaction mixture using conventional methods.

Step (3) of Reaction Scheme IV can be carried out in the same manner as step (6) of Reaction Scheme II.

The compounds of Formula I can be used in the form of acid additional salts such as hydrochlorides, dihydrogen

Reaction Scheme IV

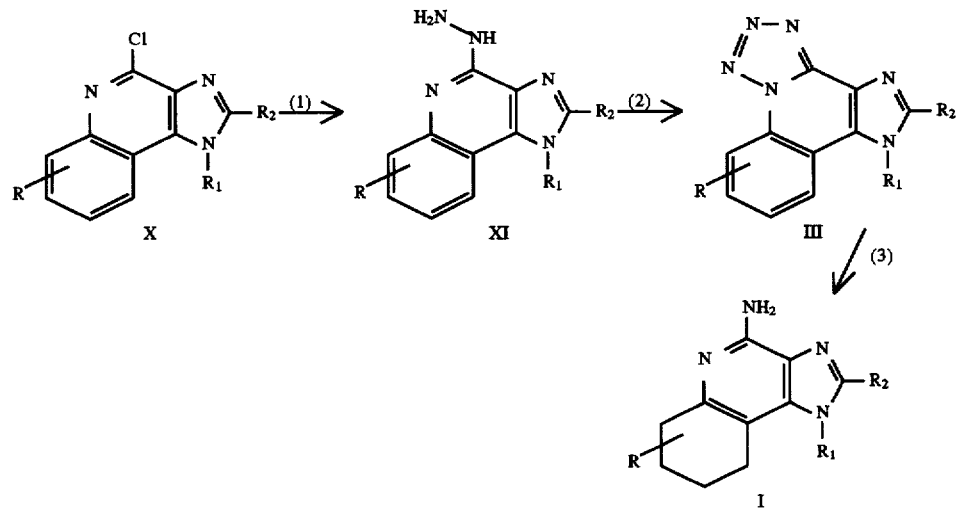

sulfates, trihydrogen phosphates, hydrogen nitrates, methane sulfonates and salts of other pharmaceutically acceptable acids. Pharmaceutically acceptable acid addition salts of Formula I are generally prepared by reaction of the respective compound with an equimolar amount of a strong acid, preferably an inorganic acid such as hydrochloric, sulfuric or phosphoric acid or an organic acid such as methanesulfonic acid in a polar solvent. Isolation of the salt is facilitated by the addition of a solvent in which the salt is insoluble (e.g., diethyl ether).

The process of the invention provide as a final product a 6,7,8,9-tetrahydro-1H-imidazo[4,5-c]quinolin-4-amine, preferred embodiments of which are represented by Formula I. Preferred $R_1$ substituents are straight chain and branched chain alkyl containing one to about eight carbon atoms and hydroxyalkyl wherein the alkyl moiety contains one to about six carbon atoms. The most preferred $R_1$ substituents are 2-methylpropyl and 2-hydroxy-2-methylpropyl. Preferred $R_2$ substituents are hydrogen, straight and branched chain alkyl containing one to about six carbon atoms, and alkoxyalkyl wherein the alkoxy moiety contains one to about four carbon atoms and the alkyl moiety contains one to about four carbon atoms. The most preferred $R_2$ substituents are hydrogen, methyl and ethoxymethyl. The preferred R substituent is hydrogen.

The 6,7,8,9-tetrahydro-1H-imidazo[4,5-c]quinolin-4-amines prepared by the processes of the invention are disclosed in U.S. Pat. No. 5,352,784 (Nikolaides) as immunomodulators.

The processes described above are illustrated in the Examples below. All parts and percentages are by weight unless otherwise indicated.

Example 1

α,α-Dimethyl-6H-imidazo[4,5-c]tetrazolo[1,5-a]quinoline-6-ethanol

A suspension of 4-chloro-α,α-dimethyl-1H-imidazo[4,5-c]quinoline-1-ethanol (1.0 g, 3.6 mmole, U.S. Pat. No. 4,689,338 Example 189 Part D) in hydrazine (3 mL, 6.9 mmole) was heated on a steam bath for 1 hour then diluted with water. The resulting precipitate was isolated by filtration. The solid was dissolved in a mixture of acetic acid (2 mL) and water (15 mL) then combined with a solution of sodium nitrite (0.5 g) in water. The resulting precipitate was isolated by filtration, washed with water and dried to provide 0.71 g of α,α-dimethyl-6H-imidazo[4,5-c]tetrazolo[1,5-a]quinoline-6-ethanol as a white solid, m.p. 246°–247° C. (shrunk at 230° C.). Analysis: Calculated for $C_{14}H_{14}N_6O$: % C, 59.96; % H, 5.00; % N, 29.77; Found: % C, 59.45; % H, 5.06; % N, 29.51.

Example 2

4-Amino-α,α-dimethyl-6,7,8,9-tetrahydro-1H-imidazo[4,5-c]quinoline-1-ethanol

A catalytic amount of platinum (IV) oxide was added to a solution of α,α-dimethyl-6H-imidazo[4,5-c]tetrazolo[1,5-a]quinoline-6-ethanol (0.40 g, 1.4 mmole, Example 1) in trifluoroacetic acid (10 mL). The mixture was hydrogenated at 50 psi ($3.44 \times 10^5$ Pa) for 48 hours. The catalyst was removed by filtration and washed with ethanol. The filtrate was concentrated under vacuum using heptane to azeotrope the trifluoroacetic acid. The resulting oil solidified on standing. The solid was dissolved in water containing enough hydrochloric acid to form a salt of the product. The aqueous solution was filtered through charcoal. The filtrate was made basic with ammonium hydroxide. The resulting precipitate was isolated by filtration and dried to provide 0.3 g of 4-amino-α,α-dimethyl-6,7,8,9-tetrahydro-1H-imidazo[4,5-c]quinoline-1-ethanol as a white solid, m.p. 259.8°–261.3° C. Analysis: Calculated for $C_{14}H_{20}N_4O$: % C, 64.59; % H, 7.74; % N, 21.52; Found % C, 64.49; % H, 7.63; % N, 21.41.

Example 3

4-Amino-α,α,2-trimethyl-6,7,8,9-tetrahydro-1H-imidazo[4,5-c]quinoline-1-ethanol

Platinum (IV) oxide (2.3 g) was added to a solution of 4-amino-α,α,2-trimethyl-1H-imidazo[4,5-c]quinoline-1-ethanol (10 g, 32 mmole, U.S. Pat. No. 5,266,575 Comparative Example C1) in trifluoroacetic acid (200 mL). The mixture was hydrogenated at 50 psi ($3.44 \times 10^5$ Pa) for 5 days. The catalyst was removed by filtration. The filtrate was concentrated under vacuum. The residue was diluted with water then combined with aqueous 10% sodium hydroxide. This mixture was stirred for one hour. A precipitate was isolated by filtration and dried to provide 9.7 g of 4-amino-α,α,2-trimethyl-6,7,8,9-tetrahydro-1H-imidazo[4,5-c]quinoline-1-ethanol as solid, m.p. 290°–292° C. Analysis: Calculated for $C_{15}H_{22}N_4O$: % C, 65.67; % H, 8.08; % N, 20.42; Found % C, 65.45; % H, 7.68; % N, 20.52.

Example 4

4-Amino-2-butyl-α,α,-dimethyl-6,7,8,9-tetrahydro-1H-imidazo[4,5-c]quinoline-1-ethanol Platinum (IV) oxide (0.3 g) was added to a suspension of 4-amino-2-butyl-α,α,-dimethyl-1H-imidazo[4,5-c]quinoline-1-ethanol (1.0 g, 3.2 mmole) in trifluoroacetic acid (20 mL). The mixture was hydrogenated at 50 psi ($3.44 \times 10^5$ Pa) for 3 days. The reaction mixture was filtered to remove the catalyst then concentrated under vacuum. The resulting residue was covered with water and aqueous sodium bicarbonate. A white solid was isolated by filtration then recrystallized for ethyl acetate. The reaction was repeated using 1.5 g of starting material. The combined products were taken up in dichloromethane, washed with 10% sodium hydroxide, dried over magnesium sulfate, then concentrated under vacuum. The material was recrystallized from ethyl acetate then from toluene to provide 1.15 g of crude product. This material was dissolved in methanol then combined first with one equivalent of hydrochloride acid then with diethyl ether. The resulting salt was converted back to the free base then purified by silica gel column chromatography diluting with 10% methanol in ethyl acetate. The resulting material was recrystallized from toluene then dried under vacuum at 110° C. to provide 0.7 g of 4-amino-2-butyl-α,α,-dimethyl-6,7,8,9-tetrahydro-1H-imidazo[4,5-c]quinoline-1-ethanol as a solid, m.p. 160°–161.5° C. Analysis: Calculated for $C_{18}H_{28}N_4O$: % C, 68.32; % H, 8.92; % N, 17.70; % C, 67.96; % H, 89.95; % N, 17.48.

Example 5

4-Amino-α,α,-dimethyl-6,7,8,9-tetrahydro-1H-imidazo[4,5-c]quinoline-1-ethanol

Platinum (IV) oxide (0.3g) was added to a suspension of 4-amino-α,α,-dimethyl-1H-imidazo[4,5-c]quinoline-1-ethanol (0.5 g, 1.95 mmole, U.S. Pat. No. 4,689,338

Example 189) in trifluoroacetic acid (15 mL). The mixture was hydrogenated at 50 psi (3.44×10$^5$ Pa) overnight. The reaction mixture was filtered to remove the catalyst then concentrated under vacuum. The residue was diluted with water then combined with aqueous sodium bicarbonate. The resulting precipitate was isolated by filtration. The nuclear magnetic resonance spectroscopy indicated the reduced product.

Example 6

2-Methyl-[(4-nitro-5-tetrazolo[1,5-a]quinolinyl) amino]-2-propanol

Sodium azide (19.5 g, 0.3 moles), 2-methyl-[(2-chloro-3-nitroquinoline-4-yl)amino]-2-propanol (29.6 g, 0.10 mole, U.S. Pat. No. 4,988,815 Example 12) and N,N-dimethylformamide (100 mL) were added to a jacketed 1 liter round bottom flask with the outside portion containing acetone. The reaction mixture was stirred with a stirring bar and the acetone refluxed to provide a constant internal reaction temperature of 53° C. After 18 hours the reaction mixture was diluted with water (100 mL). The resulting yellow precipitate was isolated by filtration then washed with 50% N,N-dimethylformamide/water until the washes became light colored. The yellow/green solid was then washed with water, pressed dry and washed with ether. The solid was air dried to provide 27.2 g of crude product as a yellow/light green solid. This material was recrystallized form ethanol/dichloromethane to provide 2-methyl-[(4-nitro-5-tetrazolo[1,5-a]quinolinyl)amino]-2-propanol as a yellow crystalline solid, m.p. 204° C. (dec.). Analysis: Calculated for: $C_{13}H_{14}N_6O_3$: % C, 51.65; % H, 4.67; % N, 27.8; Found: % C, 51.30; % H, 4.69; % N, 27.43.

Example 7

[(4-Amino-5-tetrazolo[1,5-c]quinolinyl)amino]-2-methyl-2-propanol

2-Methyl-[(4-nitro-5-tetrazolo[1,5-a]quinolinyl)amino]-2-propanol (30.2 g, 0.10 mole, Example 6), ethanol (300 mL) and 5% Pd/C (1.0 g of 50% water wet) were placed in a Paar apparatus. The mixture was hydrogenated. The mixture was diluted with dichloromethane then filtered to remove the catalyst. The filtrate was concentrated under vacuum. The crude product was recrystallized from ethanol to provide 20.5 g of [(4-amino-5-tetrazolo[1,5-c]quinolinyl) amino]-2-methyl-2-propanol as a yellow/green crystalline solid, m.p. 164°–167° C. Analysis: Calculated for $C_{13}H_{16}N_6O$: % C, 57.33; % H, 5.92; % N, 30.88; Found % C, 56.94; % H, 5.88; % N, 30.80.

Example 8

α,α-Dimethyl-6H-imidazo[4,5-c]tetrazolo[1,5-a] quinoline-6-ethanol

[(4-Amino-5-tetrazolo[1,5-c]quinolinyl)amino]-2-methyl-2-propanol (5 g, 0.18 mole, Example 7) was dissolved in triethyl orthoformate (17 g). The solution was heated at 120° C. for 20 hours. The reaction mixture was allowed to cool to ambient temperature then it was diluted with 1N hydrochloric acid. Formic acid (20 mL) was added to the mixture which was then heated at reflux for an hour. The reaction mixture was concentrated under vacuum then neutralized with sodium hydroxide. The crude product was recrystallized from ethanol/ethyl acetate to provide α,α-dimethyl-6H-imidazo[4,5-c]tetrazolo[1,5 -a]quinoline-6ethanol as a solid, m.p. 245°–248° C. Analysis: Calculated for $C_{14}H_{14}N_6O$: % C, 59.55; % H, 4.99; % N, 29.77; Found: % C, 59.44; % H, 4.93; % N, 29.65.

Example 9

Tetrazolo[1,5-a]quinolin-5-ol

Part A

Anthranilic acid (274.3 g) and acetic anhydride (1.1 L) were combined then heated at reflux for 3.5 hours. The reaction mixture was concentrated under vacuum. The residue was combined with methanol (550 mL) then concentrated under vacuum to provide 2-methyl-4oxo-3,1-benzoxazine as a brown oil.

Part B

The crude 2-methyl-4-oxo-3,1-benzoxaine was dissolved in acetic acid (1.9 L). Sodium azide (130.0 g) was added to the solution in portions with stirring. The reaction mixture was cooled in an ice bath to maintain the reaction temperature at 25° to 30° C. during the addition. The reaction mixture was allowed to stir at ambient temperature over the weekend. The acetic acid was removed under vacuum to provide a white solid. The solid was combined with 10% sodium hydroxide (1.4 L) then heated on a steam bath for 1 hour. Additional sodium hydroxide (120 g of 50% sodium hydroxide) was added. The mixture was heated on a steam bath for an additional hour then allowed to cool to ambient temperature overnight. Additional sodium hydroxide (120 g of 50% sodium hydroxide) was added. The mixture was heated on a steam bath for 2 hours then allowed to cool. The reaction mixture was poured with rapid stirring into a mixture of concentrated hydrochloric acid (1.0 L) and ice (3 L). The resulting mixture was stirred at ambient temperature overnight. A precipitate was isolated by filtration, rinsed with water then slurried with water (4 L). The solid was isolated by filtration, rinsed with water then oven dried at 50° C. to provide 278.0 g of crude 2-(5-methyl-1H-tetrazol-1-yl)benzoic acid as a tan solid, m.p. 157°–160° C. The crude material was dissolved in 10% sodium hydroxide (2.5 L). The resulting solution was heated (95°–99° C.) for 2.5 hours, cooled, then poured with vigorous stirring into a mixture of concentrated hydrochloric acid (500 mL) and ice (5 L). The resulting mixture was allowed to stir for 2 hours. The precipitate was isolated by filtration, rinsed with water, then slurried with water (3 L). The solid was isolated by filtration, rinsed with water then dried overnight at ambient temperature to provide 228 g of 2-(5-methyl-1H-tetrazol-1-yl)benzoic acid, m.p. 164°–166° C.

Part C

Acetone (3.2 L) and 2-(5-methyl-1H-tetrazol-1-yl) benzoic acid (228 g) were combined then stirred at ambient temperature for 15 minutes. Potassium carbonate (228 g) was added to the reaction mixture in a single portion. Idoethane (366.8 g) was added dropwise to the reaction mixture producing a slight exotherm. The reaction mixture was heated at reflux for about 4 hours then stirred overnight while cooling to ambient temperature. The precipitated salts were removed by filtration then rinsed with acetone. The combined filtrates were evaported under vacuum. The residue was dissolved in dichloromethane (1.5 L). The dichloromethane solution was washed with water (1.5 L), dried over magnesium sulfate then concentrated under vacuum to provide 277 g of ethyl-2-(5-methyl-1H-tetrazol-1-yl) benzoate as a white solid m.p. 98°–100° C.

Part D

Potassium ethoxide (173.5 g) was added in portions with stirring to a mixture of ethyl-2-(5-methyl-1H-tetrazol-1-yl)

benzoate (227 g) and N,N-dimethylformamide (1.6 L). The reaction mixture was cooled with an ice bath to control the resulting exotherm. The reaction mixture was stirred overnight at ambient temperature then quenched with water (17 L). The pH was adjusted to pH 5 with acetic acid (170 L). The resulting precipitate was isolated by filtration, rinsed with water then reslurried with water (2.5 L). The solid was isolated by filtration, rinsed with water then oven dried (5520 to 60° C.) for 16 hours to provide 169.0 g of a white solid. A 3.0 g sample was recrystallized from ethanol/ dichloromethane to provide tetrazolo[1,5-a]quinolin-5-ol as a white solid, m.p. 248° C. (dec). Analysis: Calculated for $C_9H_6N_4O$: % C, 58.6; % H, 3.25; % N, 30.09; Found: % C, 58.02; % H, 3.29; % N, 30.20.

Example 10

4-Nitrotetrazolo[1,5-a]quinolin-5-ol Hydrate

Tetrazolo[1,5-a]quinolin-5-ol (10 g, 54 mmole, Example 9) was suspended in acetic acid (200 mL) then warmed to 40° C. Nitric acid (4 mL of 16M, 59 mmole) was added to the reaction mixture. The reaction mixture was heated at 80° C. for 30 minutes then allowed to cool to ambient temperature. The resulting precipitate was isolated by filtration, rinsed with water then recrystallized from isopropanol/water to provide 8.1 g of 4-nitrotetrazolo[1,5-a]quinolin-5-ol hydrate as light yellow plates, m.p. 186.5°–187° C. Analysis: Calculated for $C_9H_5N_5O_3 \cdot H_2O$: % C, 43.38; % H, 2.83; % N, 28.10; Found: % C, 43.27; % H, 2.84; % N, 28.85.

Example 11

4-Nitrotetrazolo[1,5-a]quinolin-5-yl] trifluoromethanesulfonate

Triethylamine (0.6 mL, 4.32 mmole) was added to a suspension of 4-nitrotetrazolo[1,5-a]quinolin-5-ol (1.0 g, 4.32 mmoles, Example 2) in dichloromethane (20 mL). The reaction mixture was cooled to 0° C. Triflic anhydride (0.73 mL, 4.32 mmole) was added. The reaction mixture was stirred for 3 hours at 0° C. The reaction mixture was diluted with dichloromethane (50 mL), washed with 0.5N hydrochloric acid, dried over magnesium sulfate and concentrated under vacuum. The residue was combined with hexanes (100 mL), refluxed for 15 minutes and filtered. A solid percipitated from the filtrate on cooling. The solid was isolated by filtration and dried to provide 0.2 g of 4-nitrotetrazolo[1,5-a]quinolin-5-yl] trifluoromethanesulfonate as a white solid, m.p. 132°–134° C. Analysis: Calculated for $C_{10}H_{14}F_3N_5O_5S$: % C, 33.07; % H, 1.11; % N, 19.28; Found: % C, 33.19; % H, 1.28; % N, 19.6.

What is claimed is:

1. A process for preparing a compound of Formula I

wherein

R₁ is selected from the group consisting of hydrogen; cycloalkyl of three, four, or five carbon atoms; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroalkyl of one to about six carbon atoms; alkoxyalkyl wherein the alkoxy moiety contains one to about four carbon atoms and the alkyl moiety contains two to about six carbon atoms; acyloxyalkyl wherein the acyloxy moiety is alkanoyloxy of two to about four carbon atoms or benzoyloxy, and the alkyl moiety contains one to about six carbon atoms; aminoalkyl of one to about four carbon atoms; morpholinoalkyl wherein the alkyl moiety contains two to about four carbon atoms;

R₂ is selected from the group consisting of hydrogen, straight chain or branched chain alkyl containing one to about eight carbon atoms and —C(R_s)(R_t)(X)

wherein R_S and R_T are independently selected from the group consisting of hydrogen and alkyl of one to about four carbon atoms, X is selected from the group consisting of alkoxy containing one to about four carbon atoms, alkoxyalkyl wherein the alkoxy moiety contains one to about four carbon atoms and the alkyl moiety contains one to about four carbon atoms, alkylamino wherein the alkyl group contains one to about four carbon atoms, amino, substituted amino wherein the substituent is alkyl or hydroxyalkyl of one to about four carbon atoms, and morpholinoalkyl the alkyl moiety contains one to about four carbon atoms, and R is selected from the group consisting of hydrogen, straight chain or branched chain alkyl containing one to about four carbon atoms; comprising the steps of:

(i) providing a compound of Formula II

wherein R, R₁, and R₂ are as defined above;
(ii) reducing a solution or suspension of the compound of Formula II in trifluoroacetic acid in the presence of platinum (IV) oxide under hydrogen pressure;
(iii) isolating the compound of Formula I or a pharmaceutically acceptable addition salt thereof.

2. A process according to claim 1 wherein R₁ is selected from the group consisting of straight chain or branched chain alkyl containing one to about eight carbon atoms and hydroxyalkyl containing one to about six carbon atoms.

3. A process according to claim 1 wherein R₁ is 2-methylpropyl.

4. A process according to claim 1 wherein R₁ is 2-hydroxy-2-methypropyl.

5. A process according to claim 1 wherein R₂ is selected from the group consisting of hydrogen, straight chain or branched chain alkyl containing one to about four carbon atoms, and alkoxyalkyl wherein the alkoxy moiety contains one to about four carbon atoms and the alkyl moiety contains one to about four carbon atoms.

6. A process according to claim 1 wherein R₂ is selected from the group consisting of hydrogen, methyl and ethoxymethyl.

7. A process according to claim 1 wherein R is hydrogen.

8. A process for preparing a compound of Formula I

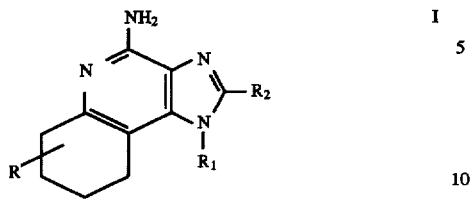

wherein

R₁ is selected from the group consisting of hydrogen; cycloalkyl of three, four, or five carbon atoms; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and Cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains two to about six carbon atoms; acyloxyalkyl wherein the acyloxy moiety is alkanoyloxy of two to about four carbon atoms or benzoyloxy, and the moiety contains one to about six carbon atoms; aminoalkyl of one to about four carbon atoms; morpholinalkyl wherein the alkyl moiety contains two to about four carbon atoms;

R₂ is selected from the group consisting of hydrogen, straight chain or branched chain alkyl one to about eight carbon atoms and —C(R$_r$)(R$_r$)(X)

wherein R$_S$ and R$_T$ are independently selected from the group consisting of hydrogen and alkyl of one to about four carbon atoms, X is selected from the group consisting of alkoxy containing one to about four carbon atoms, alkoxyalkyl wherein the alkoxy moiety contains one to about four carbon atoms and the alkyl contains one to about four carbon atoms, alkylamido wherein the alkyl group contains one to about four carbon atoms, amino, substituted amino wherein the substituent is alkyl or hydroxyalkyl of one to about four carbon atoms, and morpholinoalkyl wherein the alkyl moiety contains one to about four carbon atoms, and R is selected from the group consisting of hydrogen, straight chain or branched chain alkyl containing one to about four carbon atoms; comprising the steps of:

(i) providing a compound of Formula III

wherein R, R₁, R₂ are as defined above;

(ii) reducing a solution or suspension of the compound of Formula II in trifluoroacetic acid in the presence of platinum (IV) oxide under hydrogen pressure;

(iii) isolating the compound of Formula I or pharmaceutically acceptable addition salt thereof.

9. A process according to claim 8 wherein R₁ is selected from the group consisting of straight chain or branched chain alkyl containing one to about eight carbon atoms and hyroxyalkyl containing one to about six carbon atoms.

10. A process according to claim 8 wherein R₁ is 2-methlpropyl.

11. A process according to claim 8 wherein R₁ is 2-hydroxy-2-methylpropyl.

12. A process according to claim 8 wherein R₂ is selected from the group consisting of hydrogen, straight chain or branched chain alkyl containing one to about four carbon atoms, and alkoxyalkyl wherein the alkoxy moiety contains one to about four carbon atoms and the alkyl moiety contains one to about four carbon atoms.

13. A process according to claim 8 wherein R₂ is selected from the group consisting of hydrogen, methyl and ethoxymethyl.

14. A process according to claim 8 wherein R is hydrogen.

* * * * *

UNITED STATES PATENT AND TRADEMARK OFFICE
CERTIFICATE OF CORRECTION

PATENT NO.: 5,693,811
DATED: December 2, 1997
INVENTOR(S): Kyle J. Lindstrom

It is certified that error appears in the above-identified patent and that said Letters Patent is hereby corrected as shown below:

Title page, item [54] and Col. 1, line 2,

In the title, "TETRAHDROIMIDAZOQUINOLINAMINES" should be --TETRAHYDROIMIDAZOQUINOLINAMINES--;

Column 14, line 7, "hydroalkyl" should be --hydroxyalkyl--;

Column 14, line 26, "alkylamino" should be --alkylamido--;

Column 15, line 20, "Cycloalkyl" should be --cycloalkyl--;

Column 15, line 28, "the moiety" should be --the alkyl moiety--;

Column 15, line 42, "alkyl contains" should be --alkyl moiety contains--; and

Column 16, lines 30, "2-methlpropyl" should be --2-methylpropyl--.

Signed and Sealed this

Twentieth Day of October, 1998

Attest:

BRUCE LEHMAN

Attesting Officer

Commissioner of Patents and Trademarks